(12) United States Patent
Ippisch (10) Patent No.: US 8,866,419 B2
(45) Date of Patent: Oct. 21, 2014

(54) SURGICAL ELECTRICAL TOOL, ACTIVATION UNIT AND CALIBRATION METHOD THEREFOR

(75) Inventor: Andreas Ippisch, Merdingen (DE)

(73) Assignee: Stryker Leibinger GmbH & Co. KG, Freiburg (DE)

(*) Notice: Subject to any disclaimer, the term of this patent is extended or adjusted under 35 U.S.C. 154(b) by 2466 days.

(21) Appl. No.: 11/380,712

(22) Filed: Apr. 28, 2006

(65) Prior Publication Data

US 2007/0096666 A1 May 3, 2007

(30) Foreign Application Priority Data

Aug. 17, 2005 (DE) .................. 10 2005 038 864

(51) Int. Cl.
| | | |
|---|---|---|
| *H02P 5/50* | (2006.01) | |
| *A61B 17/16* | (2006.01) | |
| *H01H 9/02* | (2006.01) | |
| *A61B 17/00* | (2006.01) | |
| *H01H 9/04* | (2006.01) | |
| *A61C 1/00* | (2006.01) | |

(52) U.S. Cl.
CPC ...... *A61B 17/1626* (2013.01); *H01H 2300/014* (2013.01); *H01H 9/0214* (2013.01); *A61B 2017/00017* (2013.01); *H01H 9/04* (2013.01); *A61C 1/0015* (2013.01); *A61B 2017/00367* (2013.01)
USPC .......................................................... 318/71

(58) Field of Classification Search
USPC ............... 310/324, 348, 338, 339; 606/169
See application file for complete search history.

(56) References Cited

U.S. PATENT DOCUMENTS

| | | | | |
|---|---|---|---|---|
| 3,463,990 | A | | 8/1969 | Ross |
| 4,794,215 | A | * | 12/1988 | Sawada et al. ................ 200/512 |
| 5,332,944 | A | * | 7/1994 | Cline ............................ 310/339 |
| 5,561,278 | A | * | 10/1996 | Rutten ......................... 200/5 A |
| 5,982,304 | A | * | 11/1999 | Selker et al. ................... 341/27 |
| 6,003,390 | A | * | 12/1999 | Cousy ......................... 73/865.7 |
| 6,037,724 | A | * | 3/2000 | Buss et al. ..................... 318/71 |
| 6,064,141 | A | * | 5/2000 | Wiciel .......................... 310/339 |
| 6,106,524 | A | * | 8/2000 | Eggers et al. .................. 606/50 |
| 6,500,169 | B1 | * | 12/2002 | Deng ................................. 606/1 |
| 6,608,270 | B2 | * | 8/2003 | Donofrio et al. ........... 200/302.1 |
| 6,945,981 | B2 | * | 9/2005 | Donofrio et al. ............. 606/169 |
| 7,177,533 | B2 | * | 2/2007 | McFarlin et al. ............. 388/800 |

(Continued)

FOREIGN PATENT DOCUMENTS

| | | |
|---|---|---|
| CH | 674111 | 6/1984 |
| EP | 1236439 | 4/2002 |

OTHER PUBLICATIONS

Search Report Application No. 06008508.1-1526; dated Feb. 21, 2007; mailed Mar. 2, 2007.

*Primary Examiner* — Christopher Beccia
(74) *Attorney, Agent, or Firm* — Howard & Howard Attorneys PLLC (57) ABSTRACT

A sterilizable surgical power tool and an operating unit for the surgical power tool are described. The operating unit includes a hermetically sealed metal capsule for arrangement in the region of a housing of the surgical power tool, the capsule having a contact surface for a finger on an outer face. A force sensor which is in force-transmitting connection to the contact surface is arranged inside the capsule. At least one electrical contact leads out of the capsule. The capsule may be a low-cost standard transistor housing.

3 Claims, 8 Drawing Sheets

(56) References Cited

U.S. PATENT DOCUMENTS

7,358,654 B2 * 4/2008 Aromin ................. 310/348
7,398,688 B2 * 7/2008 Zdeblick et al. ............ 73/700

2002/0011092 A1 * 1/2002 Hara et al. ................. 73/1.13
2002/0049464 A1 * 4/2002 Donofrio et al. ............ 606/169
2003/0105499 A1 * 6/2003 Hartley et al. ................ 607/17
2005/0267329 A1 * 12/2005 Konstorum et al. .......... 600/112

* cited by examiner

SURGICAL ELECTRICAL TOOL, ACTIVATION UNIT AND CALIBRATION METHOD THEREFOR

FIELD OF THE INVENTION

The invention relates to a finger-force-controlled operating unit for a surgical power tool. The invention relates further to a surgical power tool having such an operating unit and to a calibration method for the power tool.

BACKGROUND OF THE INVENTION

For several decades surgical power tools have supported surgeons in their work. As examples of surgical power tools, electric-motor-driven surgical drills, bone saws and screwdrivers for bone screws may be mentioned.

Every surgical power tool includes an operating unit, for example, a movable switch or rotary knob for controlling certain functionalities of the tool. In the simplest case the operating unit may have a tumbler switch for selectively switching the power tool on and off. Multi-stage switches are frequently used, so that a user of the power tool can select between various operating modes. For adjusting a speed of the power tool, rotary operating units such as stepless rotary knobs are coming into use.

Conventional mechanical operating units, such as tumbler switches or rotary knobs, are frequently unsuitable for surgical power tools, and are certainly unsuitable if the tools must be sterilised. This is related to the fact that such operating units include a large number of mechanical moving components which are very difficult to seal to prevent ingress of liquid or gaseous sterilisation media. Ingress of a sterilisation medium into such operating units is detrimental to their operability. For this reason surgical power tools having tumbler switches, rotary knobs or similar mechanical operating units either cannot be sterilised at all or must be serviced after a few sterilisation cycles.

To improve the sterilisability of surgical power tools, or to make it possible in the first place, the mechanical operating units of such tools are frequently replaced by a combination of a force sensor and a signal processing circuit for the force sensor. Force sensors generally have a planar form and have no moving mechanical elements. For this reason force sensors can be installed in a simple and sealed manner below a flexible housing section of a surgical power tool.

Surgical power tools having a force sensor arranged below a flexible housing section are known, for example, from U.S. Pat. No. 3,463,990 and U.S. Pat. No. 6,037,724. In the case of such surgical power tools the force sensor is usually housed within a casing of plastics material which protects the force sensor (and often the associated signal processing circuit also) against a sterilisation medium. It has been found in practice, however, that despite this casing maintenance or exchange of the sensor-based operating units is necessary after only a few sterilisation cycles.

It is an object of the invention to specify an operating unit for a surgical power tool which withstands a large number of sterilisation cycles. It is further an object of the invention to provide a surgical power tool which is better able to be sterilised. A further object of the invention is to specify a calibration method for the power tool.

SUMMARY OF THE INVENTION

According to a first aspect of the invention, an operating unit for a surgical power tool is provided. The operating unit includes a hermetically sealed metal capsule for arrangement in the region of a housing of the surgical tool, the capsule defining on an outer face a contact surface for a finger. The operating unit further includes a force sensor arranged inside the capsule, which force sensor is in force-transmitting connection to the contact surface, and at least one electrical contact leading out of the capsule.

The capsule may be arranged in, on or under the housing of the surgical power tool. At least the areas of the capsule which are arranged in a region of the housing exposed to the sterilisation medium are advantageously made of a metal resistant to sterilisation media (or coated with such a metal). The capsule may be made of a metal and, if required, may have a sheath of plastics or other material. However, the capsule may also have a core made of a non-metallic material which is covered with a metal coating.

To enable the surgeon to find the operating unit even when he is not looking towards the surgical power tool, the contact surface may have a clearly defined three-dimensional boundary. The three-dimensional boundary can be detected haptically by the surgeon, thus simplifying operation of the surgical power tool.

With regard to the structure of the force sensor, a selection can be made between different implementations. For example, it is possible to configure the force sensor as a strain gauge, a piezo element, a semiconductor element, etc. The force sensor may be arranged on an inner face of the capsule opposite the contact surface. If the contact surface is formed by an upper face of a capsule wall, the force sensor may accordingly be fixed directly on an underside of the capsule wall opposite the contact surface. The force sensor may be fixed by means of bonding or in any other manner.

A signal processing circuit coupled to the force sensor is advantageously provided for the force sensor. The signal processing circuit may be arranged outside or inside the capsule. According to a first variant, the signal processing circuit taps a sensor signal and converts it into a continuous output signal dependent on the actuation force. According to a second variant, the signal processing circuit converts the sensor signal into a discrete (e.g. binary or multi-level) output signal.

The capsule may have different shapes. For example, the capsule may have a cylindrical, and in particular a short-cylindrical (pill-shaped) configuration. According to one embodiment, the capsule has a pot-shaped metallic cap and a capsule base for closing the cap. In this embodiment the contact surface is formed on an upper face of the cap or on the base of the capsule. The capsule base, located opposite the upper face of the cap, may, depending on its degree of exposure to the sterilisation medium, consist of a non-metallic material or contain a metal material.

To make possible tapping of the signal or to conduct signals outside the capsule, the capsule may have one or more openings through which the at least one electrical contact extends. The openings are preferably formed in a side wall or on an underside of the capsule and are hermetically closed. To close the openings, glass or a similarly resistant material is suitable.

The capsule for receiving the force sensor may be specially made according to the requirements of the particular surgical power tool. As a low-cost alternative, however, the capsule may also be a standard element (for example, a standard transistor housing).

According to a further aspect of the invention, a surgical power tool is provided. The surgical power tool comprises a housing, an electric motor and at least one finger-force-controlled operating unit arranged in the region of the housing and including a hermetically sealed force sensor. The operating unit has a metal housing insert which defines on an outer face a contact surface for applying force by means of a finger. The force sensor is in force-transmitting connection to this contact surface.

The housing insert may be formed by a hermetically sealed metal capsule inside which the force sensor is arranged. In this case the contact surface for force application may be provided in the form of an outer face of the capsule. However, the metal housing insert does not necessarily have an encapsulation function for the force sensor. Rather, the metal housing insert might have a substantially planar form adapted, if required, to a curvature of the housing, in which case special measures for hermetically sealing the force sensor may be necessary. Such measures may include a hermetically sealed connection of the metal housing insert to zones of the housing adjoining the housing insert. The metal housing insert may be made of a (for example, two-layered or multilayered) composite material. In this case the housing insert includes at least one metal layer.

The metal region of the housing insert which transmits the finger force to the force sensor advantageously possesses elastic (resilient) properties with respect to the finger force applied. To achieve elastic properties, the area and thickness of the metallic region may be selected suitably. With too-thick material the finger force necessary to produce a deformation detectable by the force sensor is too high. On the other hand, with a too-thin material, there is a danger that the finger force would cause non-reversible (plastic) deformation. Depending on the metal material selected, and taking account of the dimensions of the contact surfaces, a person skilled in the art will be able to select a suitable material thickness between these two limit ranges. In the case of commercially available sterilisable metal materials (e.g. NiCo steels), typical material thicknesses of finger-typical contact area sizes range from approximately 0.05 mm to 1.0 mm, advantageously approximately 0.1 to 0.4 mm.

To improve the handling of the surgical power tool, the contact surface may project above a surface of the housing or be recessed with respect to the surface. Such a measure makes it easier for the surgeon to find the contact surface haptically and therefore to operate the tool. Additionally or alternatively, the contact surface may have surface structuring (for example, in the manner of fluting).

A single power tool may include one, two or more operating units. For example, it is possible that a first operating unit is provided to control the electric motor in a first direction of rotation and a second operating unit to control the electric motor in a second direction of rotation opposite to the first.

A motor control circuit may be provided for the electric motor and a signal processing circuit for the force sensor. The signal processing circuit advantageously includes a bridge circuit which also contains the force sensor.

The surgical power tool may be a surgical drill, a surgical saw or a screwdriver (e.g. for bone screws). According to a first variant, the power tool has a pistol-shaped housing. According to a second variant, the power tool has an elongated and at least approximately cylindrical housing, the at least one operating unit being arranged in a front housing section (that is, facing towards the tool itself, such as a drill or a screwdriver bit).

According to a third aspect, the use of a metal standard transistor housing (or parts thereof) for hermetically encapsulating a force sensor for an operating unit of a surgical power tool is proposed. The standard transistor housing may be a TO8 or any other transistor housing.

According to a further aspect of the invention, a method for calibrating a force sensor, of the type that can be used in an operating unit according to the invention or in a surgical power tool according to the invention, is provided. The method comprises the steps of detecting a predetermined event, measuring an output signal of the force sensor as a response to the detection of the predetermined event, and using the measured output signal as the zero signal for the next operating process. The method is preferably carried out in the non-actuated state (without finger force application).

The predetermined event may be activation of a voltage supply of a signal processing circuit or activation of the surgical power tool itself. For example, upon switching on the power tool or upon insertion of a battery pack the above-mentioned steps may be carried out automatically. According to an alternative or additional embodiment, the predetermined event includes the expiry of a predetermined time interval without any operating process having taken place.

BRIEF DESCRIPTION OF THE DRAWINGS

Further aspects and advantages of the invention will become apparent from the following description of preferred embodiments and from the Figures, in which.

DESCRIPTION OF PREFERRED EMBODIMENTS

The invention is explained below with reference to preferred embodiments of surgical power tools and to an operating unit provided therefor. Corresponding elements are denoted by corresponding reference signs.

Figure 1:
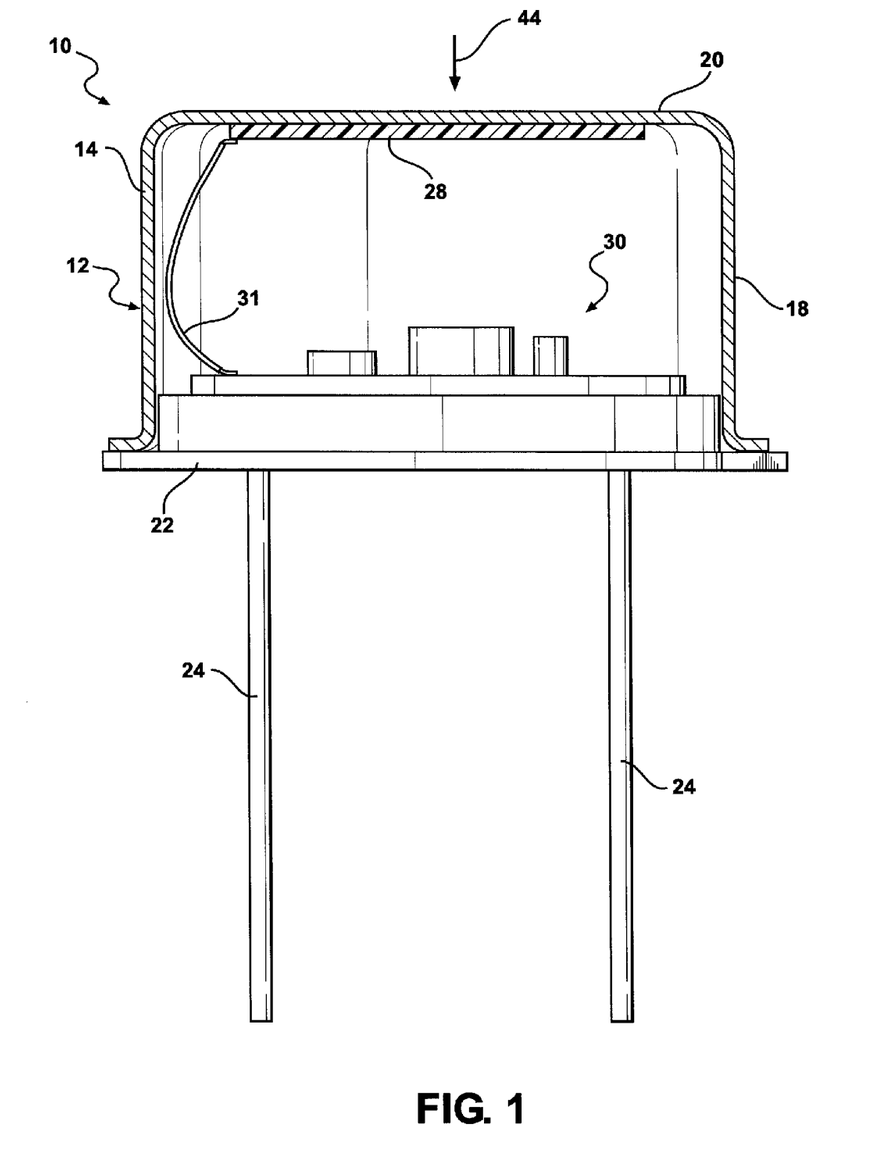
FIG. 1 is a schematic partially sectional view of a first embodiment of an operating unit.
Figure 2:
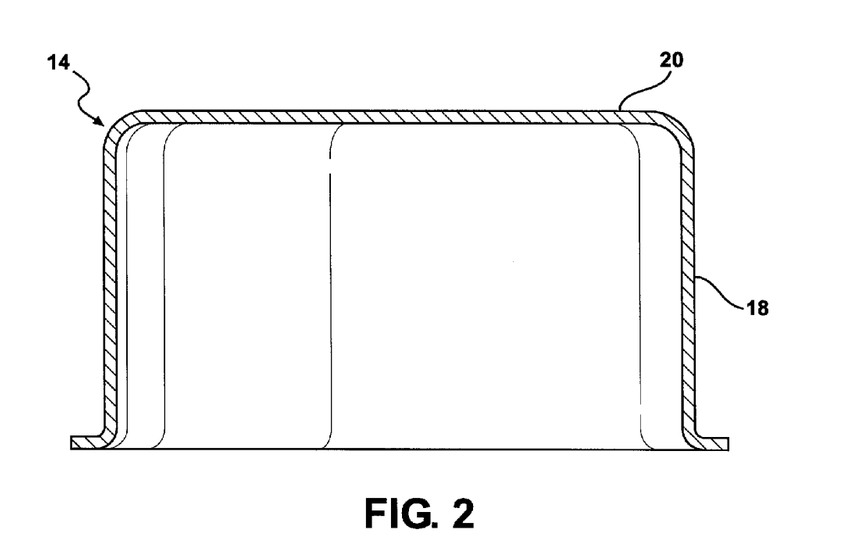
FIG. 2 is a sectional view of a cap of the operating unit according to FIG. 1.

FIG. 1 is a sectional view of a first embodiment of an operating unit 10 for a surgical power tool. The operating unit 10 includes a hermetically sealed capsule 12 in the form of a TO8 transistor housing. The capsule 12 has a substantially pot-shaped cap 14 of special steel, which is shown in FIG. 2 in a greatly enlarged sectional view. The cap 14 includes a cylindrical wall section 18 and a cover section 20 formed in one piece with the wall section 18. The internal diameter of the wall section 18 is approximately 11 mm (typically approximately 5 to 30 mm) and the height of the wall section 18 is approximately 7 mm (typically approximately 2 to 12 mm). In the Figures the cover section 20 closes the end of the wall section 18 and has a material thickness of approximately 0.25 mm. The open end of the cap 14 is closed hermetically by a cap base 22. The cap base 22 is made of a NiCo steel.

Figure 3:
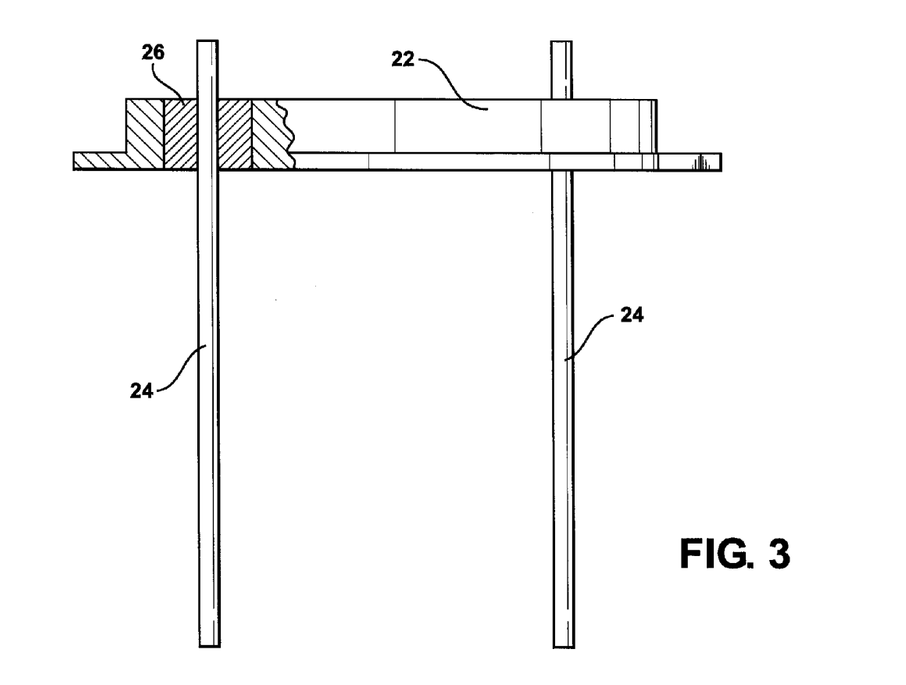
FIG. 3 shows a base part for the cap according to FIG. 2 with contacts, in a partially sectional view.
Figure 4:
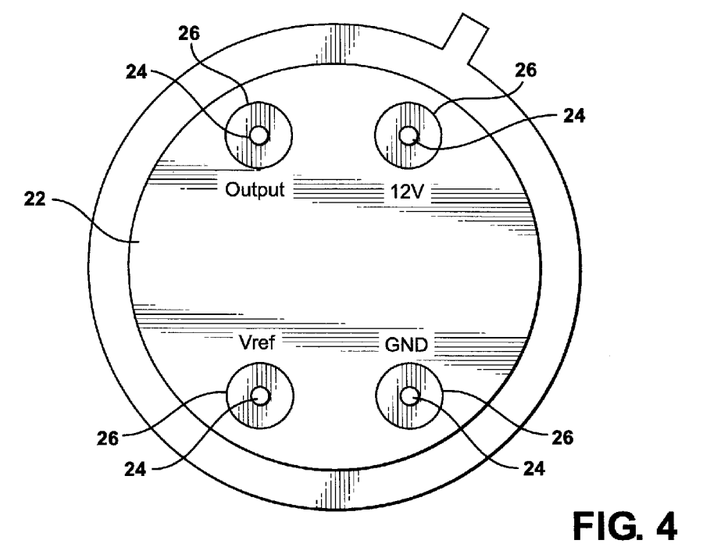
FIG. 4 is a top view of an underside of the base part according to FIG. 3 with contact labelling.

As can be seen in FIGS. 3 and 4, a total of four openings 26 are formed in the cap base 22. A gold-plated electrical contact 24 extends through each opening 26. To stabilise the contacts 24 and also to provide a high degree of sealing, the openings 26 are hermetically closed with glass.

A force sensor in the form of a strain gauge 28 and a signal processing circuit 30 for the force sensor 28 are housed inside the capsule 12. This arrangement of elements can be seen in FIG. 1. The force sensor 28 is coupled to the signal processing circuit 30 by means of electrical contacting 31. The signal processing circuit 30 is in turn electrically contacted by the contacts 24 leading out of the capsule 12.

Figure 5:
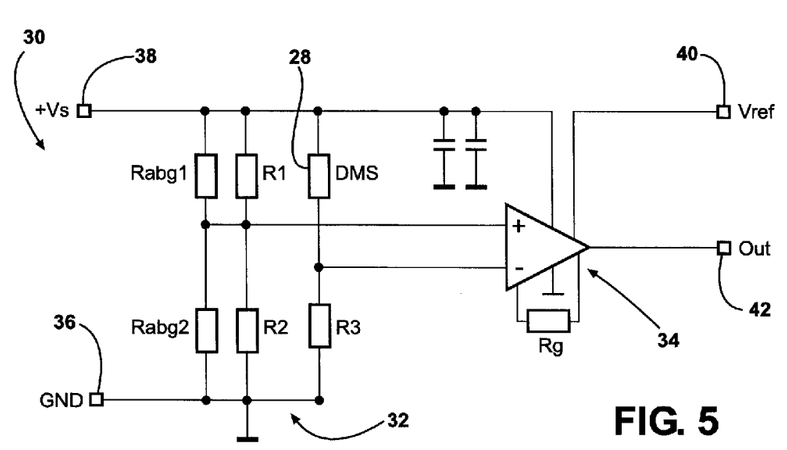
FIG. 5 is a schematic view of a signal processing circuit for the operating unit.

FIG. 5 shows a circuit diagram of the signal processing circuit 30. Essential components of the signal processing circuit 30 are a temperature-compensating resistance bridge circuit 32 and an amplifier component 34. The force sensor 28 forms part of the bridge circuit 32, which includes two balancing resistors Rabg1, Ragb2 in addition to three further bridge resistors R1, R2 and R3. Corresponding to the four contacts 24 leading out of the capsule 12 (see FIG. 4), the signal processing circuit 30 includes four connections, a ground connection 36, the connection 38 for a supply voltage, a connection 40 for a reference voltage and a connection 42 for an output signal of the amplifier component 34.

The operation of the operating unit 10 will now be explained with reference to FIGS. 1 and 5. The upper face of the cap cover 20 acts as a contact surface for a finger and allows an actuating force to be applied in the direction of the arrow 44 in FIG. 1. When an actuating force is applied to the cap cover 20 in the direction of the arrow 44, the cap cover 20 deforms elastically towards the interior of the capsule 12. This deformation of the cap cover 20 is transmitted to the force sensor 28 which is fixed, for example, by means of bonding, to the underside of the cap cover 20. More precisely, the deformation causes stretching of the force sensor 28 configured as a strain gauge. As a result of this stretching the resistance of the force sensor 28 changes. This change of resistance of the force sensor 28 in turn shifts the operating point of the bridge circuit 32.

The shift of the operating point is detected by the amplifier component 34 in the form of a differential amplifier and converted into an amplified difference signal. The amplified difference signal is supplied for further processing to the connection 42 as the output signal of the signal processing circuit 30. The level of the output signal is proportional to the deformation of the strain gauge force sensor 28 and therefore proportional to the actuating force applied to the cap cover 20. In an alternative embodiment the signal processing circuit is so configured that the output signal has two or more discrete levels (for example, in dependence on exceeding of one or more force thresholds).

Figure 6:
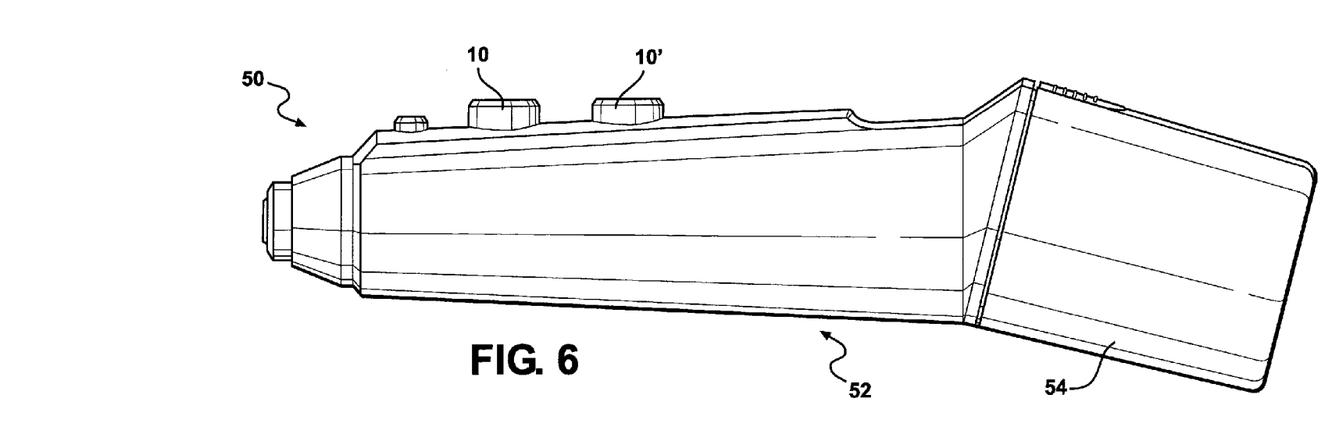
FIG. 6 is a side view of a first embodiment of a surgical power tool.
Figure 7:
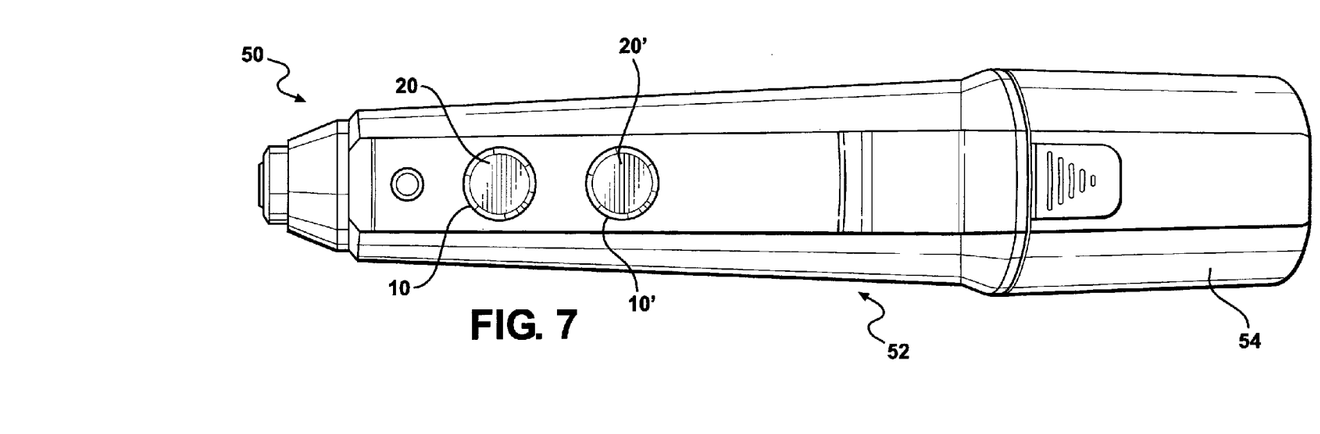
FIG. 7 is a top view of the surgical power tool according to FIG. 6.

A first embodiment of a surgical power tool 50 in the form of a battery-powered screwdriver will now be explained with reference to FIGS. 6 to 8. The surgical power tool 50 has an elongated, approximately cylindrical housing 52 into which a battery pack 54 can be plugged removably.

The surgical power tool 50 includes a total of two operating units 10, 10'. The operating units 10, 10' are formed in a front region of the housing 52 oriented away from the battery pack 54 and have the structure explained with reference to FIGS. 1 to 5. As can be seen in particular in FIG. 8, the caps of the operating units 10, 10' extend through openings provided for them in the housing 52, so that the respective cap cover 20, 20' projects somewhat above the housing 52. However, it would be possible for the upper faces of the operating units 10, 10' to be disposed in the same plane as the surface of the housing 52 or to be recessed with respect to this surface.

Figure 8:
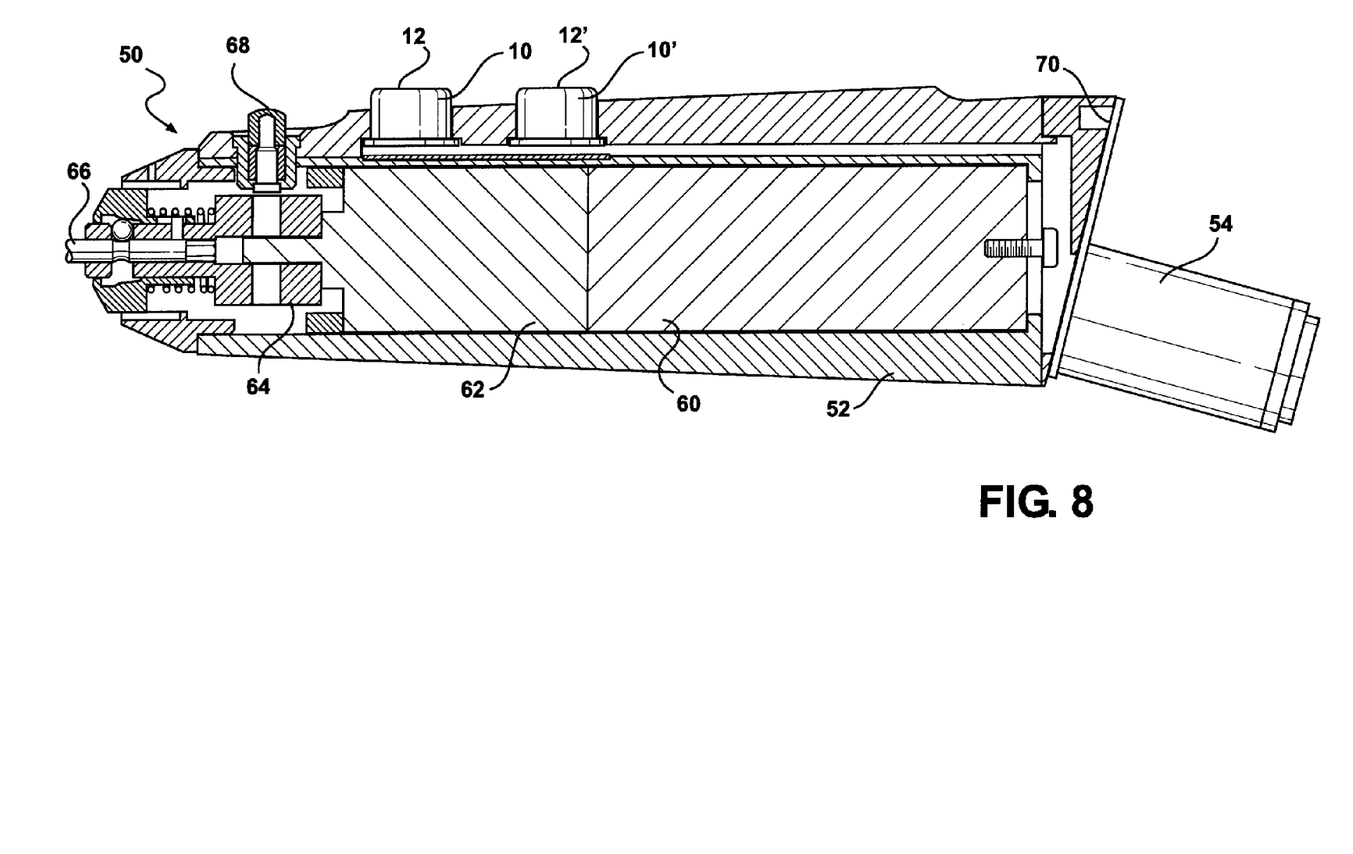
FIG. 8 is a sectional view of the surgical power tool according to FIG. 6.

As shown in FIG. 8, an electronically commutated motor 60, a transmission 62 coupled to the motor and a coupling 64 at the output of the transmission are housed inside the housing 52. The coupling 64 permits in known fashion the non-rotatable coupling of an exchangeable screwdriver bit 66 to the transmission 62. A locking button 68 also extending through the housing 52 enables non-rotatable mechanical locking of the coupling 64. When the locking button 68 is actuated the power tool 50 can be used in the manner of a conventional screwdriver (in this case torque is not generated by the motor 60 but by manual rotation of the housing 52).

As already explained, the surgical power tool 50 includes a total of two operating units 10, 10'. A first of the two operating units 10, 10' controls the electric motor 60 in a first direction of rotation ("forward direction"). The other operating unit controls the electric motor 60 in a second direction of rotation ("reverse direction") opposite to the first. The motor speed in the forward and reverse directions is proportional to the actuation force applied to the respective operating unit 10, 10'. The higher the actuating force, the higher the motor speed. To regulate the speed a motor control circuit is mounted on a printed circuit board 70 fixed in the rear portion of the housing 52.

Figure 9:
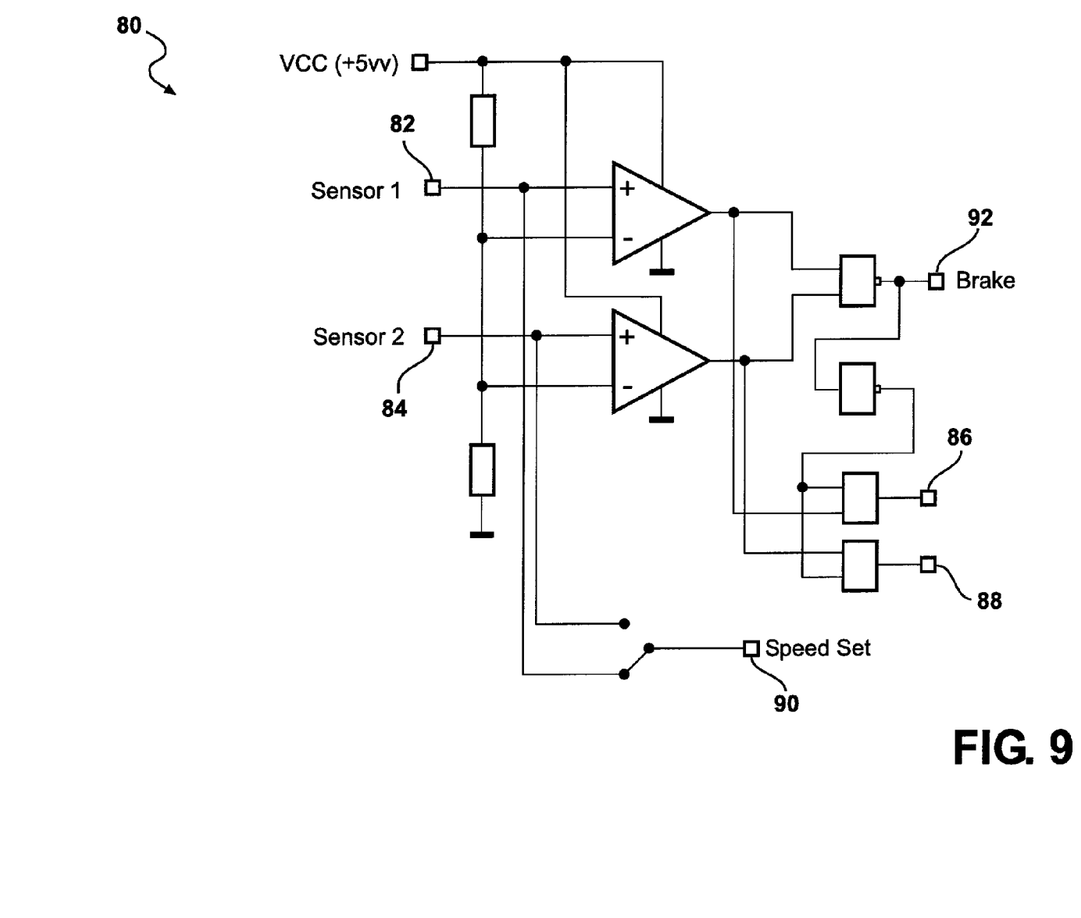
FIG. 9 shows a logic circuit for use with the surgical power tool according to FIGS. 6 and 7.

The motor control circuit is electrically coupled to the signal processing circuits of the operating units 10, 10'. The logic circuit 80 shown in FIG. 9 is arranged functionally between the motor control circuit and the two operating units 10, 10'. The logic circuit 80 has essentially the effect that with simultaneous application of force to both operating units 10, 10' no undefined state is produced. For this purpose the logic circuit has two separate input connections 82, 84, each of which is coupled to one of the two operating units 10, 10'. If a signal is supplied to only one of the two input connections 82, 84, an amplified output signal is transmitted to the motor control circuit via exactly one of the two output connections 86, 88. A signal for the first direction of rotation is supplied to the motor control circuit via contact 86 and a signal for the second, opposite direction of rotation via contact 88.

If output signals are supplied to both input connections 82, 84 of the logic circuit 80 (i.e. if an actuating force is applied to both operating units 10, 10'), the logic implemented in the logic circuit 10 causes no output signal to be sent from either of the two output connections 86, 88 to the motor control circuit. In addition, the "brake" connection 92 adopts a high signal level. The high signal level at connection 92 short-circuits the electronically commutated electric motor 60, whereby the electric motor 60 is electrically braked and brought to a standstill.

The logic circuit 80 shown in FIG. 9 also includes a speed control connection 90. Via the speed control connection 90 the motor control circuit receives a feedback message regarding the required motor speed.

The surgical power tool 50 described with reference to FIGS. 6 to 9 withstands an extremely large number of sterilisation cycles in an autoclave. A reason for this is the impermeability to a sterilisation medium of the operating units 10, 10' with the force sensors encapsulated in each of their metal cases. A further advantage is that despite high resistance to a sterilisation medium the operating units 10, 10' are not necessarily integrated in a planar manner in the housing 52, but may project above the housing 52. This permanently facilitates handling of the surgical power tool 52, since the surgeon can "feel" the operating units 10, 10' without difficulty. The surgical power tool 52 can therefore be operated without visual contact.

Further embodiments of an operating unit 10 according to the invention and of a power tool 50 according to the invention will now be discussed with reference to FIGS. 10 to 13. The embodiments of FIGS. 10 to 13 correspond in essential aspects to the embodiments explained above. For this reason corresponding elements are denoted by corresponding reference signs.

Figure 10:
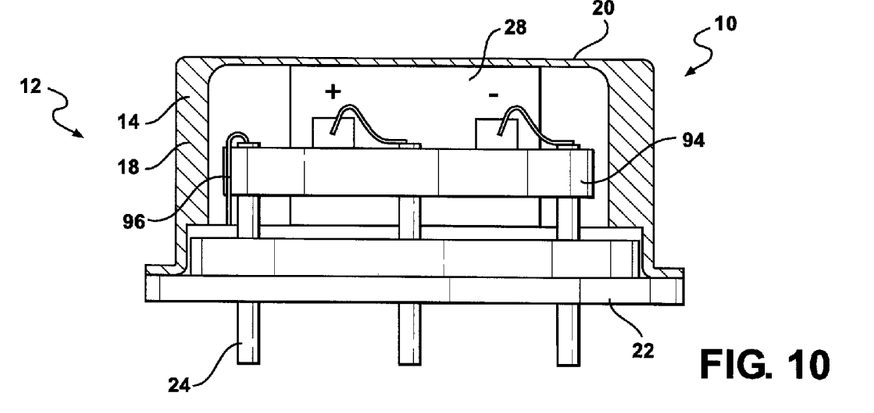
FIG. 10 is a schematic partially sectional view of a second embodiment of an operating unit.

FIG. 10 shows a sectional view of a second embodiment of an encapsulated operating unit 10 for a surgical power tool. A printed circuit board 94 of a signal processing circuit is housed inside the capsule 12. The signal processing circuit is electrically connected to the cap base 22 via a ground connection 96. While the cap 14 of the capsule 12 is in any case a specially-made item, the base 22 may originate from a TO8 transistor housing.

Figure 11:
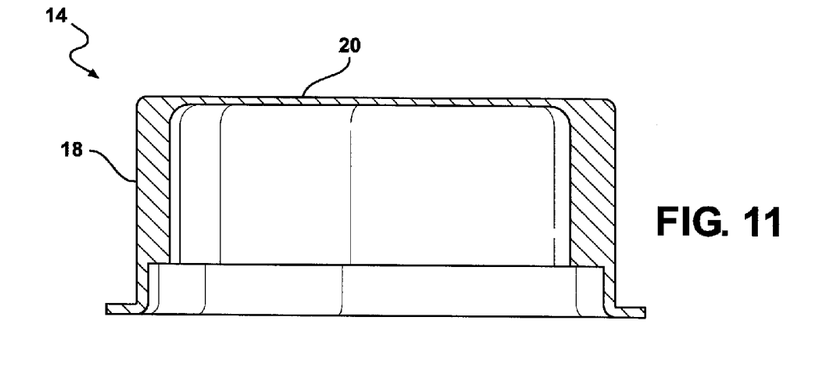
FIG. 11 is a sectional view of a cap of the operating unit according to FIG. 10.

The sectional view according to FIG. 11 of the cap 14 made of special steel shows the differences from the first embodiment. A major difference is that the cylindrical wall section 18 has significantly greater material thickness than the cover section 20. While the cover section has a thickness of approximately 0.3 mm, the wall section 18 has a thickness of at least approximately 0.8 mm or more. Such a configuration is advantageous in restricting to the cover section 20 the elastic deformations resulting from application of a finger force to the cover section 20. In other words, the wall section 18 behaves in a substantially rigid manner with respect to actuation forces applied to the cover section 20. This facilitates the hermetically sealed installation of the operating unit 10 in the housing of an electric power tool.

Figure 12:
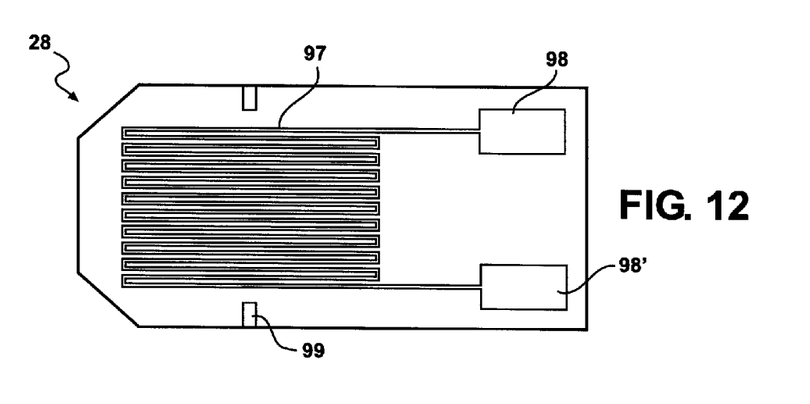
FIG. 12 is a top view of a strain gauge used in the operating unit according to FIG. 10.

FIG. 12 shows a top view of the force sensor 28 housed in the capsule 12 according to FIG. 10. The force sensor 28 comprises a serpentine structure 97 of a strain gauge strip having two contacts 98, 98'. In the installed, finished state the contacts 98, 98' are electrically connected to the signal processing circuit. Two markings 99 indicate the centre of the serpentine structure 97 and thus allow centred installation within the capsule 12. Assembly can be effected by bonding.

Figure 13:
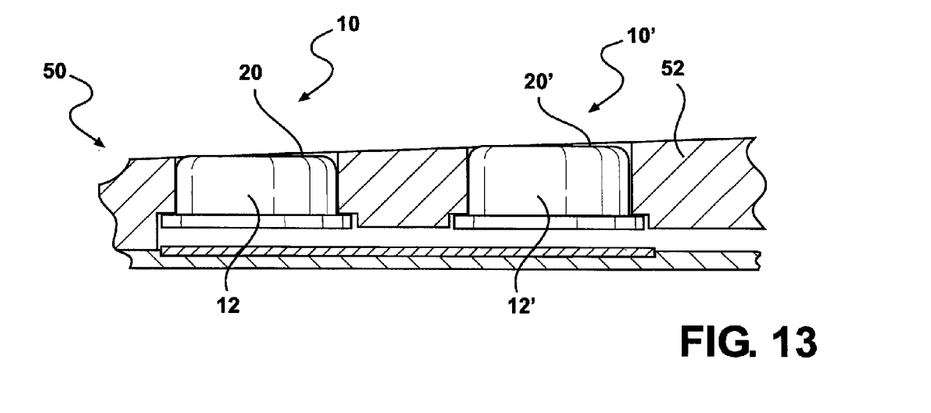
FIG. 13 is a sectional view of a portion of a second embodiment of a surgical power tool.

FIG. 13 shows a partially sectional view of a surgical power tool 50 according to a second embodiment. The two operating units 10, 10', which are configured as in the embodiment explained with reference to FIGS. 10 to 12, can be clearly seen. According to FIG. 13, the upper cover sections 20, 20' (i.e. the contact surfaces) end flush with an upper face of the housing 52 of the power tool 50.

An embodiment of a calibration method for the force sensors 28 of the surgical power tool 50 according to FIGS. 6 to 9 and 13 is explained below with reference to the flow chart 100 of FIG. 14. However, this calibration method can be used quite generally in power tools which include an operating unit 10 according to FIGS. 1 to 5 or 10 to 12. The method is advantageously stored in the form of a software program in the power tool concerned.

Figure 14:
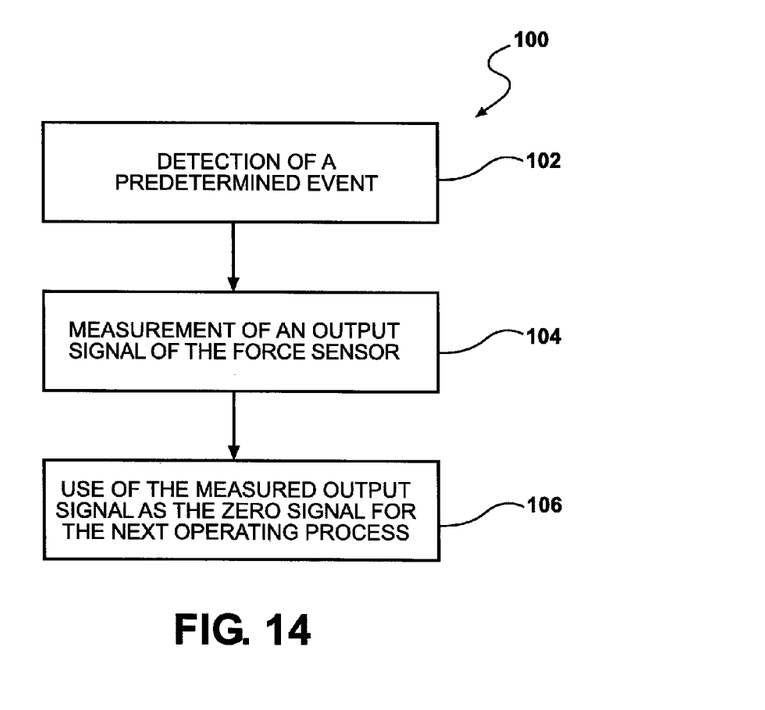
FIG. 14 is a schematic flow chart of an embodiment of a calibration method.

As shown in FIG. 14, the method begins in a first step 102 with the detection of a predetermined event. This predetermined event may be the attachment of the battery pack 54 to the surgical power tool 50 and the accompanying activation of the voltage supply. Additionally or alternatively, the predetermined event may be the expiry of a predetermined time interval (of typically 10 seconds to 60 seconds, e.g. 30 seconds) in which neither of the operating units 10, 10' has been activated.

In the next step 104 the output signal of each force sensor 28 is measured for a brief period of typically 0.5 seconds to 5 seconds (e.g. for about 1 hour).

In a further step 106 the measured output signal is set as the zero signal for the following operating process. The zero signal, which corresponds to non-actuation of the operating units 10, 10', is therefore continuously updated.

Such continuous updating of the zero signal has various advantages, in particular in conjunction with the operating units explained herein. For example, permanent (plastic) mechanical deformations of the metal capsule 12, as may be caused by impacts on or dropping of the power tool 50, are automatically compensated. Furthermore, material fatigue effects and deformations can be reliably counteracted. The surgical power tool 50 therefore remains continuously operable and controllable. Moreover, the power tool 50 is maintenance-free because the operating units 10, 10' contain no moving parts and require no re-adjustment. The associated advantages are considerable, above all, in a surgical environment.

Self-evidently, the field of application of the operating unit according to the invention is not limited to a surgical power tool in the form of a screwdriver. Rather, an operating unit according to the invention can also be used in other surgical power tools, such as drills, saws, etc.

Numerous modifications and additions relating to the operating unit according to the invention and to the surgical power tool according to the invention are therefore possible. The scope of the invention is limited only by the scope of protection of the following claims.

The invention claimed is:

1. A method of calibrating a force sensor for a surgical tool, comprising the steps:
   providing the surgical tool with the force sensor for use in a surgical procedure;
   detecting activation of the surgical tool during the surgical procedure;
   detecting an expiry of a predetermined time interval when the surgical tool is inactive during the surgical procedure;
   measuring an output signal of the force sensor as a response to the detection of the expiry of the predetermined time interval when the surgical tool is inactive; and
   utilizing the measured output signal of the force sensor as a zero signal for a next activation of the surgical tool.

2. A method for calibrating a force sensor of a surgical tool, comprising the steps:
   providing the surgical tool with the force sensor for use in a surgical procedure;
   detecting a predetermined event of the surgical tool, wherein the predetermined event is an activation of a voltage supply;
   measuring an output signal of the force sensor as a response to the detection of the predetermined event; and
   utilizing the measured output signal as a zero signal for a next operating process.

3. A method for calibrating a force sensor of a surgical tool, comprising the steps:
   providing the surgical tool with the force sensor for use in a surgical procedure;
   detecting a predetermined event of the surgical tool, wherein the predetermined event is an expiry of a predetermined time interval of from 10 seconds to 60 seconds during which no operating process has taken place;
   measuring an output signal of the force sensor as a response to the detection of the predetermined event; and
   utilizing the measured output signal as a zero signal for a next operating process.

* * * * *